(12) United States Patent
Rezach et al.

(10) Patent No.: US 12,414,802 B2
(45) Date of Patent: Sep. 16, 2025

(54) SURGICAL INSTRUMENT AND METHOD

(71) Applicant: WARSAW ORTHOPEDIC INC., Warsaw, IN (US)

(72) Inventors: William Alan Rezach, Covington, TN (US); Brian A. Butler, Millington, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 680 days.

(21) Appl. No.: 17/846,419

(22) Filed: Jun. 22, 2022

(65) Prior Publication Data

US 2022/0387084 A1 Dec. 8, 2022

Related U.S. Application Data

(63) Continuation of application No. 17/078,648, filed on Oct. 23, 2020, now abandoned.

(51) Int. Cl.
*A61B 17/88* (2006.01)
*A61B 17/00* (2006.01)
*A61B 17/70* (2006.01)

(52) U.S. Cl.
CPC .... *A61B 17/7082* (2013.01); *A61B 17/00234* (2013.01)

(58) Field of Classification Search
CPC ............ A61B 17/7082; A61B 17/7076
USPC ................ 606/86 A, 99, 104, 265
See application file for complete search history.

(56) References Cited

U.S. PATENT DOCUMENTS

| | | | |
|---|---|---|---|
| 9,615,862 B1* | 4/2017 | Doubler | A61B 17/7076 |
| 2010/0030278 A1* | 2/2010 | Hawkes | B25B 13/44 |
| | | | 606/301 |
| 2011/0098755 A1* | 4/2011 | Jackson | A61B 17/8685 |
| | | | 606/305 |
| 2014/0066993 A1* | 3/2014 | Kwak | A61B 17/7037 |
| | | | 606/279 |
| 2018/0325558 A1* | 11/2018 | Yacoub | A61B 17/8816 |

* cited by examiner

*Primary Examiner* — Eduardo C Robert
*Assistant Examiner* — David C Comstock
(74) *Attorney, Agent, or Firm* — Sheridan Ross P.C.

(57) ABSTRACT

A surgical instrument includes a first member being engageable to an inner surface of a spinal implant. An actuator is connected to a second member such that the second member is translatable relative to the first member for connecting the spinal implant to a bone fixation device. Systems, spinal constructs, implants and methods are disclosed.

20 Claims, 16 Drawing Sheets

SURGICAL INSTRUMENT AND METHOD

CROSS REFERENCE TO RELATED APPLICATIONS

This application is a continuation of U.S. patent application Ser. No. 17/078,648, filed Oct. 23, 2020, which is expressly incorporated by reference herein, in its entirety.

TECHNICAL FIELD

The present disclosure generally relates to medical devices for the treatment of musculoskeletal disorders, and more particularly to a surgical system and a method for treating a spine.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment of implants to the exterior of two or more vertebral members. This disclosure describes an improvement over these prior technologies.

SUMMARY

In one embodiment, a surgical instrument is provided. The surgical instrument includes a first member being engageable to an inner surface of a spinal implant. An actuator is connected to a second member such that the second member is translatable relative to the first member for connecting the spinal implant to a bone fixation device. In some embodiments, systems, spinal constructs, implants and methods are disclosed.

In one embodiment, the surgical instrument includes an outer sleeve including a distal portion having at least one spring tab biased radially inward and expandable for engagement to an inner surface of a spinal implant. An inner shaft includes a distal portion and a handle is connected to the inner shaft such that the distal portion of the inner shaft is translatable relative to the distal portion of the outer sleeve for connecting the spinal implant to a bone fastener shaft.

In one embodiment, a surgical system is provided. The surgical system includes a bone fastener shaft configured for fixation to vertebral tissue. A spinal implant receiver is configured for connection to the bone fastener shaft. A surgical instrument includes a first member that is engageable to an inner surface of the spinal implant receiver and a second member. The surgical instrument further includes an actuator connected to the second member such that the second member is translatable relative to the first member for connecting the spinal implant receiver to the bone fastener shaft.

BRIEF DESCRIPTION OF THE DRAWINGS

The present disclosure will become more readily apparent from the specific description accompanied by the following drawings, in which.

DETAILED DESCRIPTION

Figure 1:
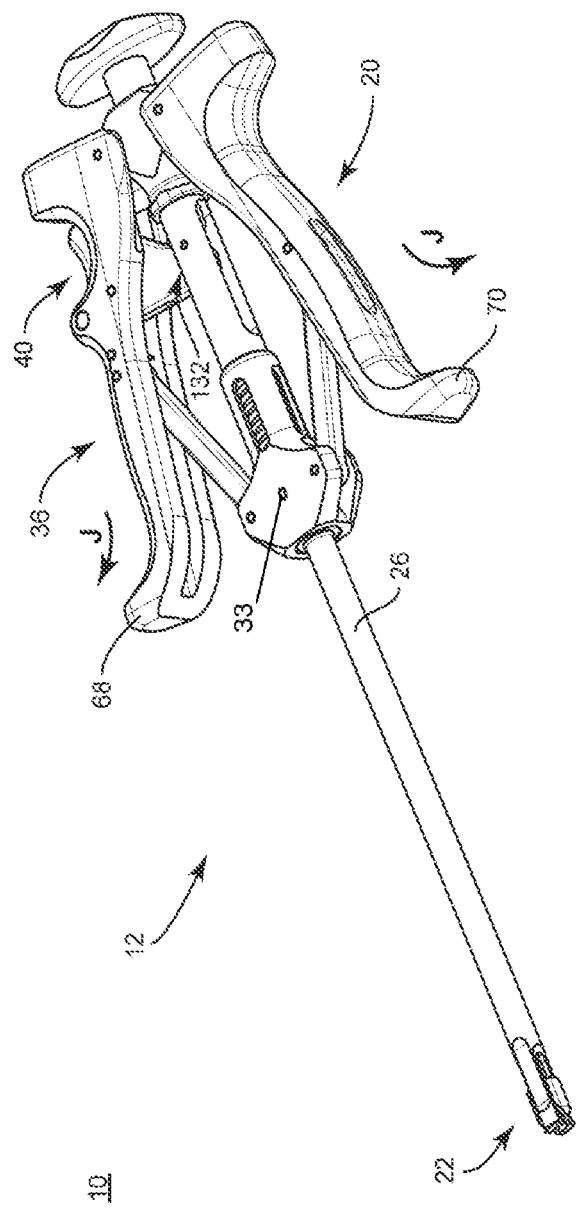
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system includes a surgical instrument, for example, an inserter engageable to a spinal implant, for example, a receiver. In some embodiments, the present surgical system includes an inserter having an end engageable to an inner surface of a spinal implant to capture and connect the spinal implant to a bone fixation device, including a bone fastener shaft.

In some embodiments, the present surgical system includes a surgical instrument, for example, an inserter configured to connect a spinal implant to a bone fixation device, including a bone fastener shaft. In some embodiments, the inserter includes an outer sleeve, an inner shaft and an actuator. In some embodiments, the actuator is connected to the inner shaft such that the inner shaft is translatable relative to the outer sleeve for connecting the spinal implant to the bone fastener shaft. In some embodiments, the inserter is configured to connect a spinal implant to bone fixation devices, including bone screws, hooks and/or plates.

In some embodiments, the present surgical system includes a surgical instrument, for example, an inserter configured for utilization with a modular screw platform. In some embodiments, the modular screw platform includes a plurality of spinal implants, for example, a plurality of receivers having a plurality of heights and/or a plurality of external geometries. In some embodiments, an end of the inserter is configured to engage to the plurality of receivers. In some embodiments, the end of the inserter engages rocker holes of the receiver via an inner surface of the receiver to secure the receiver to the end of the inserter.

In some embodiments, the present surgical system includes a surgical instrument, for example, an inserter having an outer sleeve and an inner shaft with a low profile configuration. In some embodiments, the low profile configuration includes an end of the inserter configured to fit within a profile of a spinal implant, for example, a receiver to secure the receiver to the end of the inserter. In some embodiments, a profile of the spinal implant includes an interior surface that defines an internal groove. In some embodiments, the internal groove is disposed proximal to a receiver crown. In some embodiments, the outer sleeve engages the internal groove to secure the inserter to the receiver.

In some embodiments, the present surgical system includes a surgical inserter configured for securement to a spinal implant receiver. In some embodiments, the inserter includes an outer sleeve, an inner shaft and an actuator. In some embodiments, the outer sleeve includes an end including spring tabs that are biased radially inward and are expandable to engage to an inner surface of the receiver. In some embodiments, to secure the inserter to the receiver, the receiver is loaded to the distal end of the inserter. In some embodiments, the spring tabs are bent inwardly to enable the inserter to pass through the receiver. In some embodiments, the spring tabs are bent inwardly to enable the inserter to pass through a minor diameter of a thread of the inner surface of the receiver. In some embodiments, the spring tabs are heat treated in a bent position to bias the spring tabs inwardly into a closed position. In some embodiments, the receiver is secured to the inserter. In some embodiments, the inner shaft is translated toward the distal end of the inserter to deploy the spring tabs in an outward direction. In some embodiments, deployment of the spring tabs in the outward direction engages the spring tabs to the inner surface of the receiver to secure the receiver to the inserter. In some embodiments, the receiver is locked to the inserter. In some embodiments, the inner shaft is translatable through the spring tabs to push a crown of the spinal implant in a downward direction to engage a head of a screw shaft.

In some embodiments, the present surgical system includes a surgical inserter configured for securement to a spinal implant receiver. In some embodiments, the inserter includes a first member and a second member. In some embodiments, the first member includes an outer sleeve and the second member includes an inner shaft. In some embodiments, the inserter includes an actuator, for example, a pair of handles. In some embodiments, the actuator is connected to the inner shaft such that the inner shaft is translatable relative to the outer sleeve for securing the receiver to a bone fixation device, including a bone fastener shaft. In some embodiments, the inserter includes a latch, for example, a locking mechanism including a finger engagement surface. In some embodiments, the latch is connected to the actuator in at least one non-locked orientation such that the actuator is movable relative to the inner shaft and a locked orientation such that the actuator is fixed relative to the inner shaft. In some embodiments, the actuator is movable between positions such that the inserter can be secured and unsecured to the inserter. In some embodiments, the actuator is movable between an open position including the non-locked orientation, an intermediate position including the locked orientation and a closed position including the non-locked orientation. In some embodiments, the actuator translates the inner shaft relative to the outer sleeve via a threaded engagement.

In some embodiments, the actuator is oriented in the open position. In some embodiments, in the open position, the receiver is loaded into the distal end. In some embodiments, in the open position, the receiver can be loaded and/or removed from the distal end of the inserter. In some embodiments, in the open position, spring tabs of the outer sleeve are in a flexed inward state such that the spring tabs can be inserted into the interior features of the receiver. In some embodiments, in the open position, the spring tabs are in a collapsed inward state to slide through a minor diameter of an interior of the receiver.

In some embodiments, the actuator is oriented in the intermediate position. In some embodiments, in the intermediate position, the actuator is locked until the latch is manually depressed by a user. In some embodiments, the latch locks onto a pin that is centrally disposed on a shaft of the member to prevent the actuator from opening or closing. In some embodiments, in the intermediate position, the receiver is secured to the end of the inserter. In some embodiments, in the intermediate position, the outer sleeve remains fixed and the inner shaft translates in a direction, for example, axially. In some embodiments, the inner shaft translates a distance of, for example 2.0 to 3.0 mm. In some embodiments, the actuator is released to disconnect the receiver from the distal end. In some embodiments, the spring tabs are forced in an outward orientation by translation of the inner shaft to engage to the interior features of the receiver.

In some embodiments, the actuator is oriented in the closed position. In some embodiments, the latch is depressed and the actuator is compressed to position the inserter in the locking orientation to lock the receiver to the distal end. In some embodiments, in the closed position, the actuator is released when the actuator is compressed. In some embodiments, in the closed position, the outer sleeve remains fixed and the inner shaft translates in a direction, for example, axially. In some embodiments, the inner shaft translates a distance of 6.0 mm. In some embodiments, in the closed position, the receiver is secured to the end of the inserter via the spring tabs that remain in the outward orientation as the inner shaft translates axially beyond the spring tabs. In some embodiments, a tip of the inner shaft pushes an implant crown in a downward direction and into the receiver.

In some embodiments, the present surgical system includes a surgical inserter employed with a method for connecting a spinal implant receiver to a bone fixation device, including a bone fastener shaft. In some embodiments, the method includes the step of introducing an inserter. In some embodiments, the inserter includes a proximal end and a distal end. In some embodiments, the inserter includes an outer sleeve, an inner shaft, a latch and an actuator. In some embodiments, the method includes the step of disposing the inserter in an initial open position to load an implant, for example, a receiver to the distal end. In some embodiments, in the open position, the receiver is loaded into the distal end. In some embodiments, the method includes the step of disposing the inserter in an intermediate position to secure the receiver to the distal end. In some embodiments, in the intermediate position, the actuator is locked until the latch is manually depressed by a user. In some embodiments, the method includes the step of disposing the inserter into a closed position to lock the receiver to the distal end. In some embodiments, in the closed position, the actuator is released when the actuator is compressed.

In some embodiments, the system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other ostial and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Figures 3, 4:
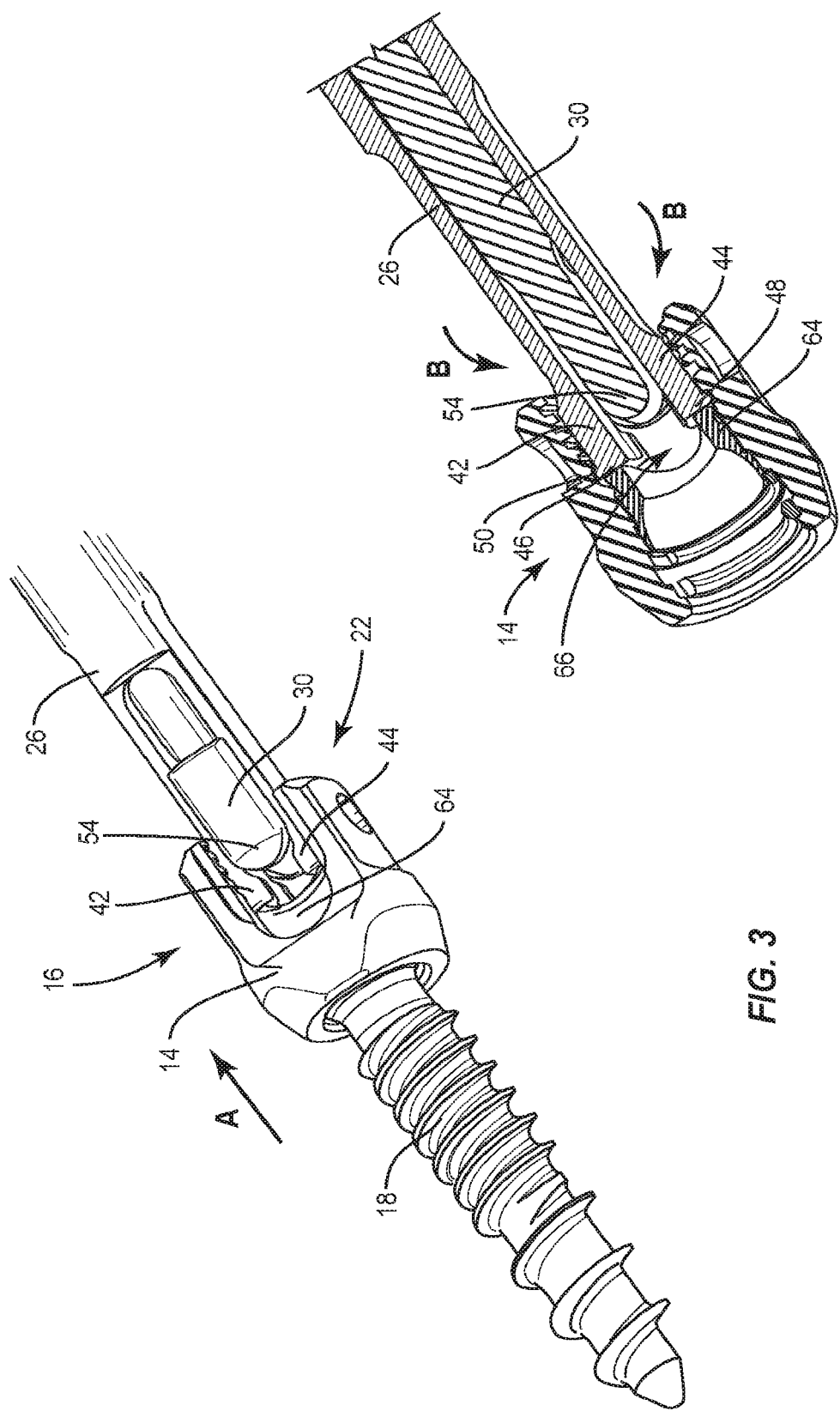
FIG. 3 is a break away view of components of one embodiment of a surgical system in accordance with the principles of the present disclosure.
FIG. 4 is a break away cross section view of components of one embodiment of a surgical system in accordance with the principles of the present disclosure.

Surgical system 10 includes a surgical instrument, for example inserter 12. Inserter 12 is configured for engagement to a spinal implant, for example, a receiver 14 of a bone fastener 16, as shown in FIG. 3. Inserter 12 is configured to secure receiver 14 to a bone fixation device, including shaft 18 of bone fastener 16 that has been implanted into a surgical site, for example, vertebral tissue, as described herein. Inserter 12 is configured for utilization with a modular screw platform such that inserter 12 can be implemented with various embodiments of receiver 14.

Figure 2:
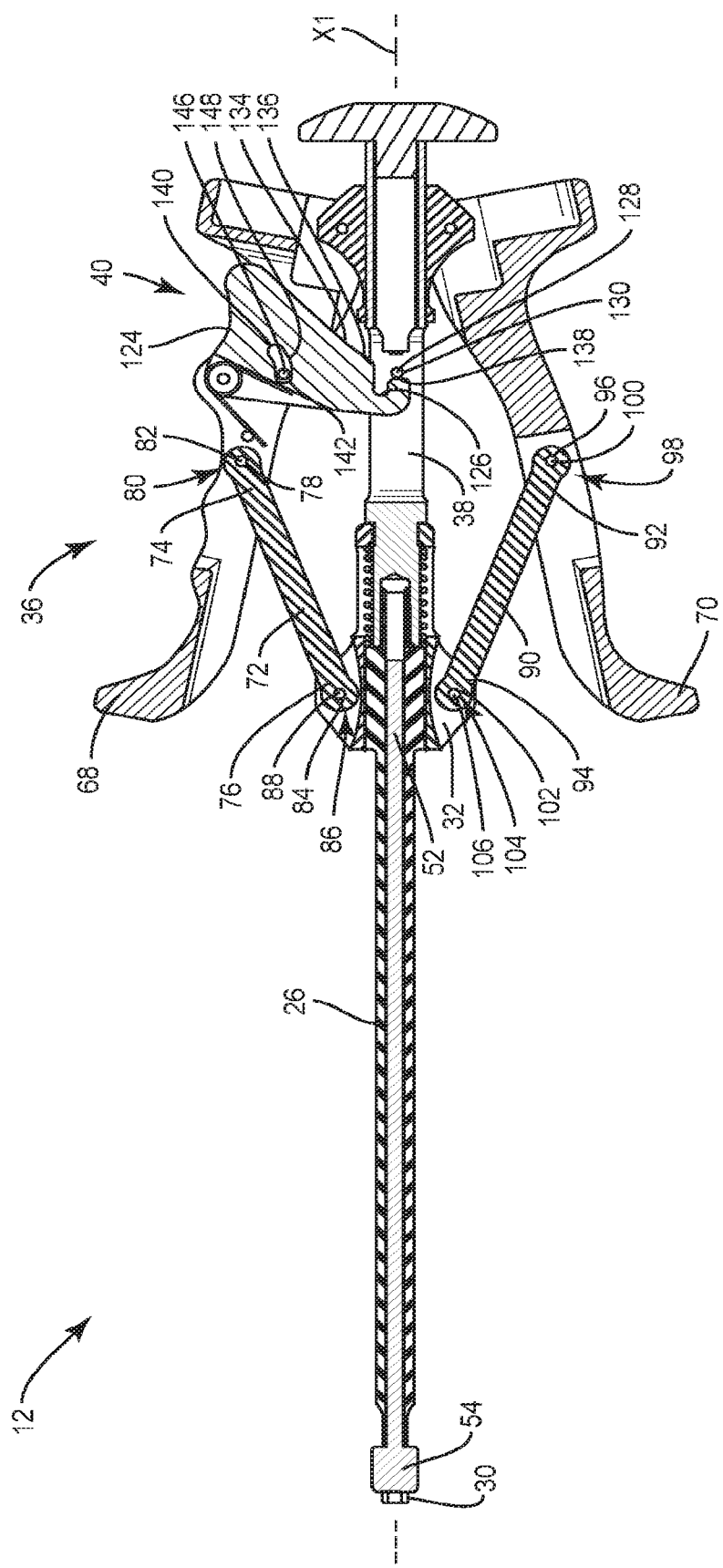
FIG. 2 is a side cross section view of the components shown in FIG. 1.

Inserter 12 includes a proximal end 20 and a distal end 22, as shown in FIG. 1. Inserter 12 extends along and defines a longitudinal axis X1, as shown in FIG. 2. In some embodiments, inserter 12 may have various cross-section configurations, for example, oval, oblong, triangular, rectangular, square, polygonal, irregular, uniform, non-uniform, variable, tubular and/or tapered.

Figure 5:
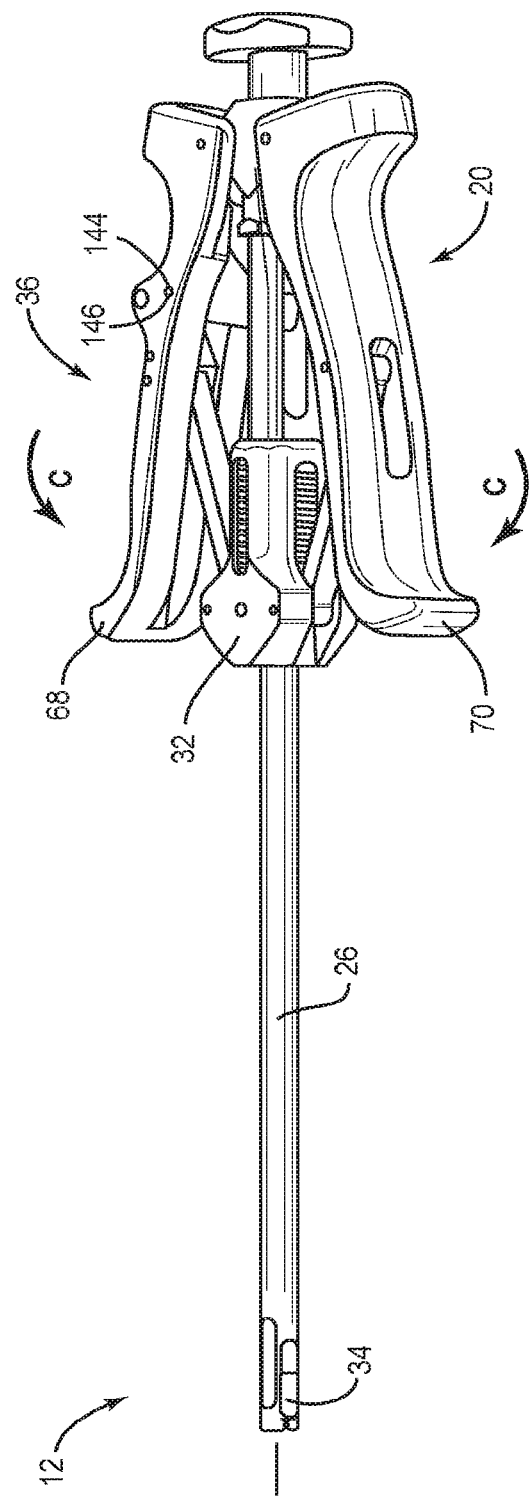
FIG. 5 is a perspective view of the components shown in FIG. 1.

Inserter 12 includes a member having an outer sleeve 26 and a member having an inner shaft 30, as shown in FIGS. 3 and 4. Sleeve 26 and shaft 30 are configured for engagement to receiver 14. Sleeve 26 is configured for engagement to an inner surface of receiver 14, as described herein. Sleeve 26 includes an end 34, as shown in FIG. 5. In some embodiments, sleeve 26 may have various cross-section configurations, for example, oval, oblong, triangular, rectangular, square, polygonal, irregular, uniform, non-uniform, variable, tubular and/or tapered.

An end 32 is configured for engagement to an actuator 36, as shown in FIG. 1. An outer shaft 38 is disposed at end 32 and is configured for engagement to actuator 36 and a latch 40, as shown in FIG. 2 and described herein. Latch 40 is connected to actuator 36 such that actuator 36 is movable relative to sleeve 26. See also, for example, the embodiments and disclosure of an inserter and method for surgically treating a spine, shown and described in commonly owned and assigned U.S. patent application Ser. No. 17/078,631 filed Oct. 26, 2020, and published as U.S. Patent Application Publication No. 20220125487, on Apr. 28, 2022, the entire contents of which being incorporated herein by reference. In some embodiments, shaft 38 may have various cross-section configurations, for example, oval, oblong, triangular, rectangular, square, polygonal, irregular, uniform, non-uniform, variable, tubular and/or tapered.

End 34 is configured for engagement to an inner surface of receiver 14, as shown in FIGS. 3, 4, 7, 8, 12 and 13. End 34 is expandable to engage the inner surface of receiver 14 to secure receiver 14 to inserter 12. End 34 includes a spring tab 42 and a spring tab 44. Tab 42 opposes tab 44. Tabs 42 and 44 are flexible, biased radially inward and are expandable to engage the inner surface of receiver 14 and to secure receiver 14 to inserter 12. Tab 42 includes an outer surface that defines a projection 46 and tab 44 includes an outer surface that defines a projection 48, as shown in FIG. 4. The inner surface of receiver 14 defines a groove 50 configured for engagement to projections 46 and 48, as shown in FIG. 4. In some embodiments, sleeve 26 includes one or more spring tabs.

Shaft 30 includes an end 52 and an end 54, as shown in FIG. 2. Shaft 30 is in co-axial alignment relative to sleeve 26 and extends along longitudinal axis X1, as shown in FIG. 2. Shaft 30 translates relative to sleeve 26 to secure receiver 14 to shaft 18, as shown in FIGS. 3, 4, 7, 8, 12 and 13. Shaft 30 is configured to expand sleeve 26 into engagement to the inner surface of receiver 14 to secure receiver 14. In some embodiments, shaft 30 may have various cross-section configurations, for example, oval, oblong, triangular, rectangular, square, polygonal, irregular, uniform, non-uniform, variable, tubular and/or tapered.

Figure 6:
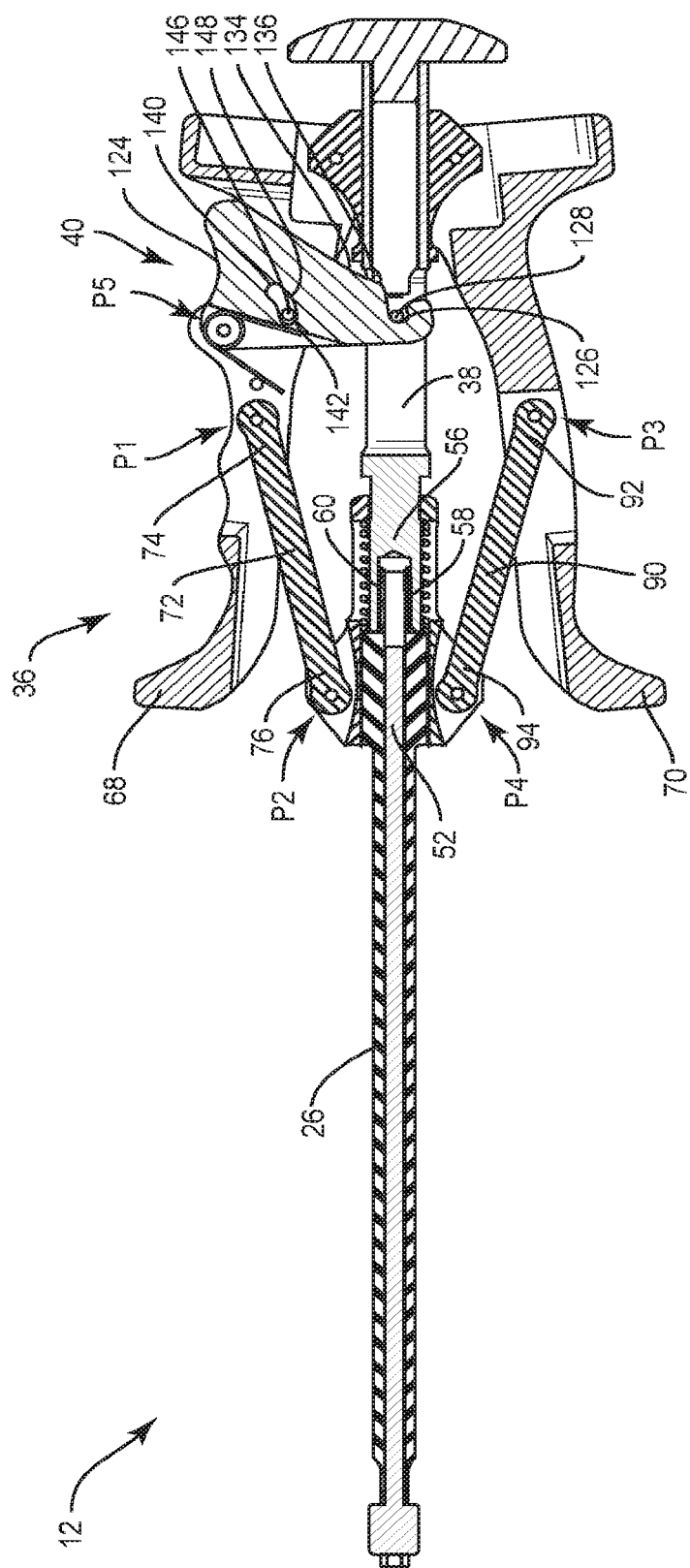
FIG. 6 is a side cross section view of the components shown in FIG. 1.
Figure 8:
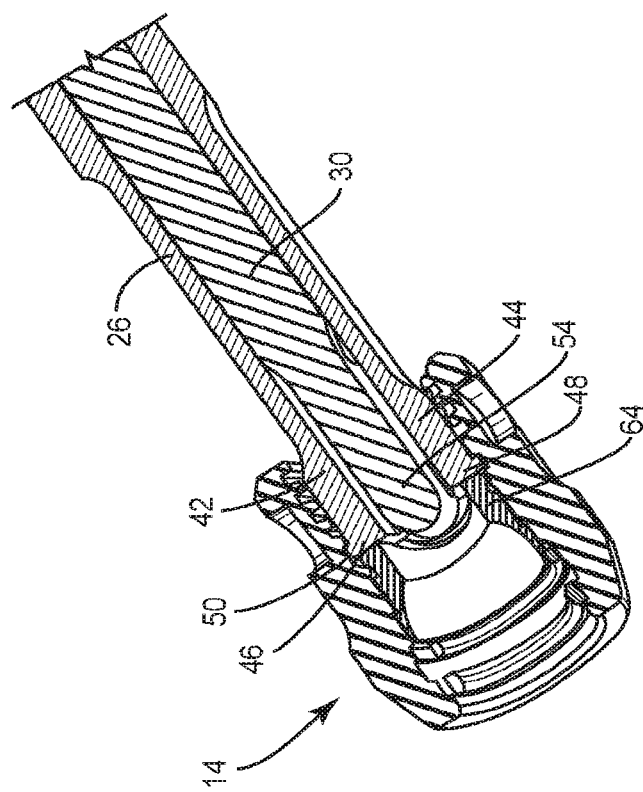
FIG. 8 is a cross section view of the components shown in FIG. 7.
Figure 9:
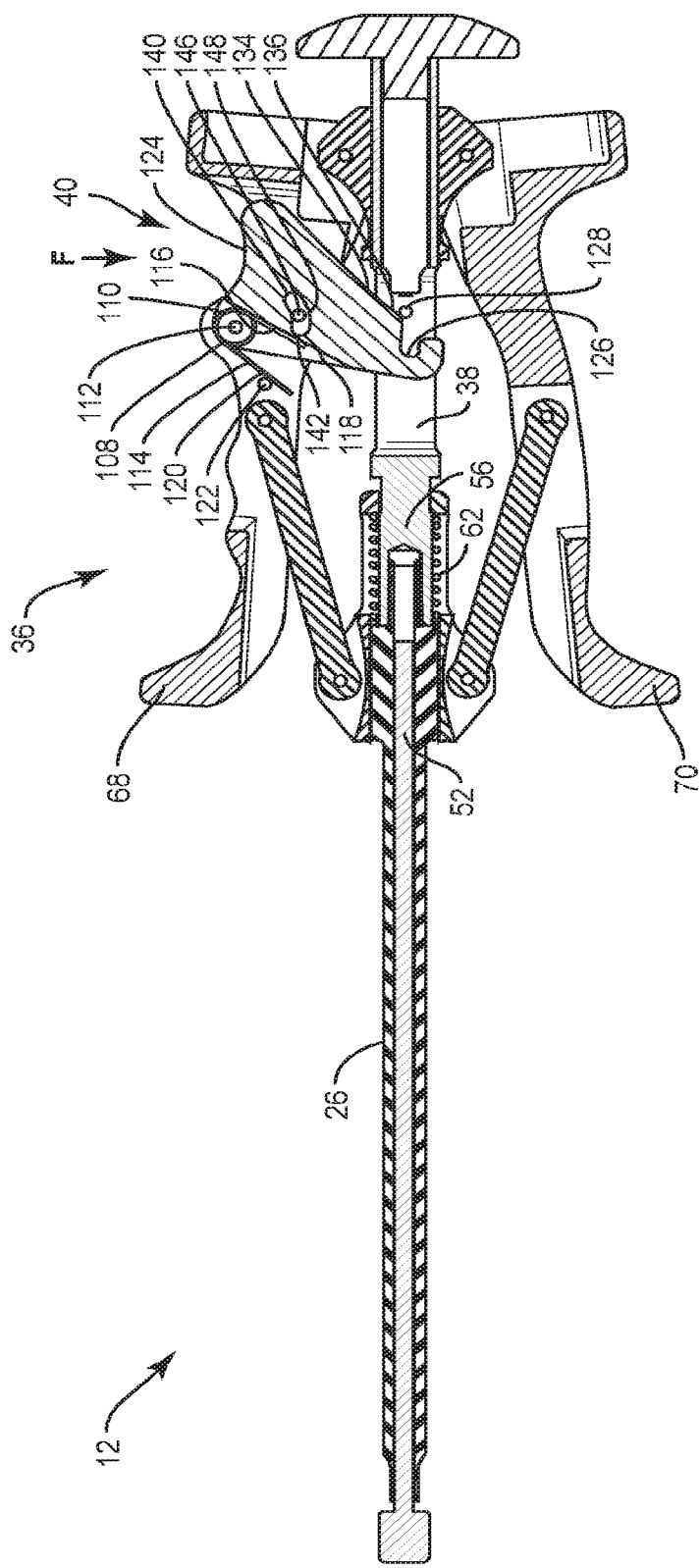
FIG. 9 is a side cross section view of the components shown in FIG. 1.

Sleeve 26 is configured for engagement to an end 56 of shaft 38, as shown in FIG. 6. Sleeve 26 includes a threaded portion 58 that is configured for disposal into a threaded recess 60 of end 56, as shown in FIG. 6. Sleeve 26 is fixed to shaft 38. Shaft 30 is fixed with end 32 via a pin 33 and movable relative to sleeve 26, as shown in FIGS. 1, 2, 6, 9 and 11. A biasing member, for example, a spring 62 is configured for disposal about end 56, as shown in FIG. 9 and is configured to provide energy in an axial direction to facilitate movement of shaft 30 when actuator 36 is released, as described herein.

Figure 7:
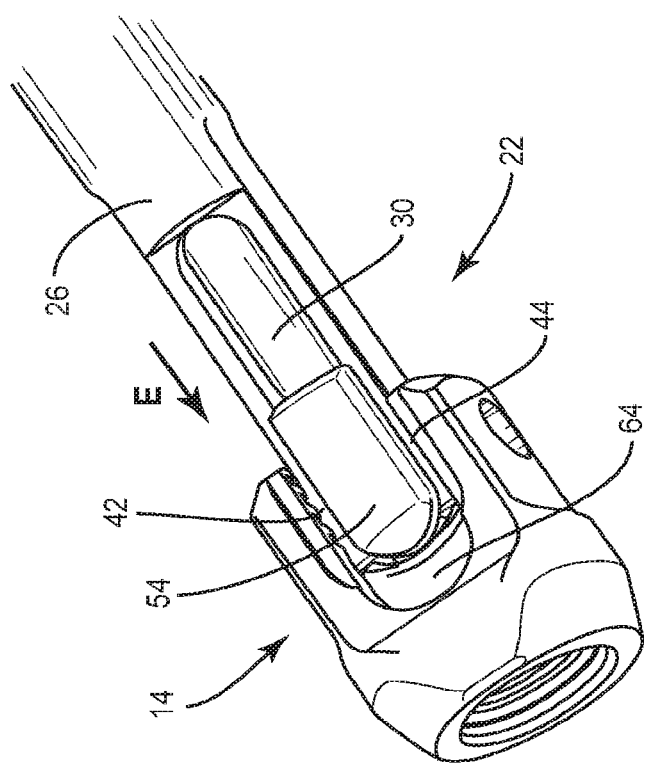
FIG. 7 is a break away view of components of one embodiment of a surgical system in accordance with the principles of the present disclosure.
Figure 12:
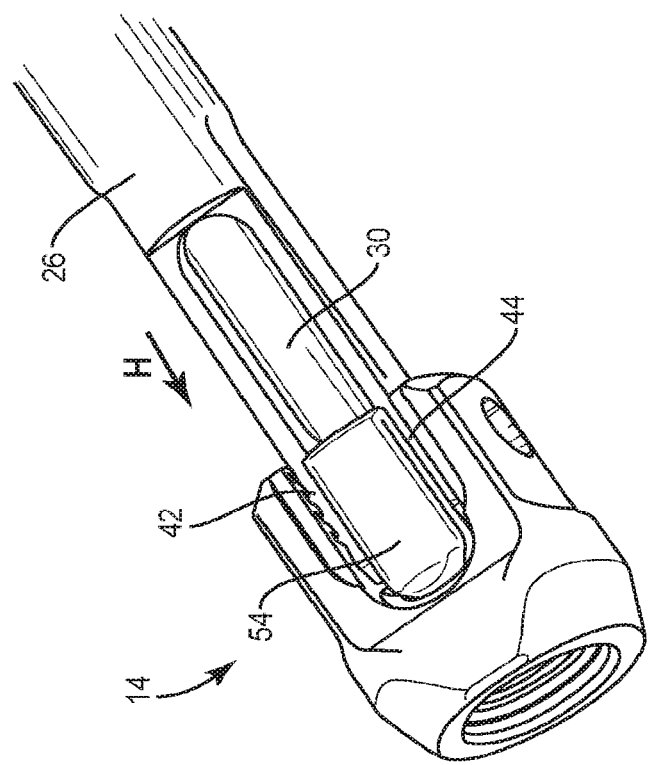
FIG. 12 is a break away view of components of one embodiment of a surgical system in accordance with the principles of the present disclosure.

End 54 is configured for engagement to a crown 64 disposed within a cavity 66, as shown in FIG. 4, of receiver 14, as shown in FIGS. 3, 7 and 12. Crown 64 is configured for locking receiver 14 to shaft 18 in a snap fit assembly, as described herein. In some embodiments, end 54 may have various cross-section configurations, for example, oval, oblong, triangular, rectangular, square, polygonal, irregular, uniform, non-uniform, variable, tubular and/or tapered.

End 20 of inserter 12 includes actuator 36, as shown in FIG. 1. Actuator 36 is connected to shaft 30 such that shaft 30 translates relative to sleeve 26 for connecting receiver 14 to shaft 18. Actuator 36 is rotatable relative to sleeve 26 and is disposable between an open position including a non-locked orientation such that actuator 36 is movable relative to sleeve 26 (FIGS. 1 and 2), an intermediate position including a locked orientation such that actuator 36 is fixed relative to sleeve 26 (FIGS. 5 and 6) and a closed position including a non-locked orientation such that actuator 36 is movable relative to sleeve 26 (FIGS. 10 and 11), as described herein. In a natural state, actuator 36 is biased to the open position and is automatically movable from the closed position to the open position.

Actuator 36 includes a pair of lever handles 68, 70, as shown in FIG. 2 that are rotatable relative to sleeve 26. In some embodiments, handles 68, 70 may have various cross-section configurations, for example, oval, oblong, triangular, rectangular, square, polygonal, irregular, uniform, non-uniform, variable, tubular and/or tapered. In some embodiments, an outer surface of handles 68, 70 has one or more of various surface configurations, for example, rough, threaded, arcuate, undulating, porous, semi-porous, dimpled, polished and/or textured. In some embodiments, actuator 36 includes one or more handles.

Handle 68 includes a bar linkage 72 that is rotatably engaged to end 32, as shown in FIG. 2. Linkage 72 includes an end 74 and an end 76. End 74 includes a surface that defines an opening 78. A surface of handle 68 defines an opening 80. End 74 engages handle 68 via a pin 82 that is disposed within openings 78 and 80. End 76 includes a surface that defines an opening 84. A surface of end 32 defines an opening 86. End 76 engages end 32 via a pin 88 that is disposed within openings 84 and 86. Engagement between end 74 of linkage 72 and handle 68 creates a pivot point P1, as shown in FIG. 6. Engagement between end 76 of linkage 72 and end 32 creates a pivot point P2, as shown in FIG. 6.

Handle 70 includes a bar linkage 90 rotatably engaged to end 32, as shown in FIG. 2. Linkage 90 includes an end 92 and an end 94. End 92 includes a surface that defines an opening 96. A surface of handle 70 defines an opening 98. End 92 engages handle 70 via a pin 100 that is disposed within openings 96 and 98. End 94 includes a surface that defines an opening 102. A surface of end 32 defines an opening 104. End 94 engages end 32 via a pin 106 that is disposed within openings 102 and 104. Engagement between end 92 of linkage 90 and handle 70 creates a pivot point P3, as shown in FIG. 6. Engagement between end 94 of linkage 90 and end 32 creates a pivot point P4, as shown in FIG. 6.

Latch 40 is connected to actuator 36 in a non-locked orientation (FIGS. 1-2 and 10-11) such that actuator 36 is movable relative to sleeve 26 in the open position and the closed position, and a locked orientation (FIGS. 5 and 6) such that actuator 36 is fixed relative to sleeve 26 in the intermediate position. Latch 40 is connected to actuator 36 via handle 68, as shown in FIG. 2. A surface of handle 68 defines an opening 108 and a surface of latch 40 defines an opening 110, as shown in FIG. 9. A pin 112 is configured for disposal within openings 108 and 110 to rotatably engage latch 40 with handle 68. Engagement between handle 68 and latch 40 creates a pivot point P5, as shown in FIG. 6. A biasing member, for example, a torsion spring 114 is configured for disposal with pin 112 and engagement to latch 40, as shown in FIG. 9. Spring 114 is configured to provide torque to latch 40 when pivoted into a non-locked and/or a locked orientation. An end 116 of spring 114 is configured for engagement to an indent 118 of latch 40 and an end 120 of spring 114 is configured for engagement to a pin 122, as shown in FIG. 9.

Latch 40 includes an outer surface that defines a trigger 124 including a finger engagement surface, as shown in FIG. 2. Trigger 124 is configured for engagement with a user such that latch 40 can be manually depressed to rotatably translate latch 40 into a selected orientation, as described herein. In some embodiments, the finger engagement surface can have one or more various surface configurations, for example, rough, threaded, arcuate, undulating, porous, semi-porous, dimpled, polished and/or textured.

Latch 40 includes a surface that defines a slot 126 configured for engagement to a pin 128 disposed in a cavity 130 of shaft 38. Latch 40 is rotatable relative to actuator 36 for capture of shaft 30 in the intermediate position such that pin 128 is disposed in slot 126 in a locked orientation, as shown in FIG. 6 and described herein. In some embodiments, slot 126 includes a C-groove configuration. In some embodiments, slot 126 may have various cross-section configurations, for example, oval, oblong, triangular, rectangular, square, polygonal, irregular, uniform, non-uniform, variable, tubular and/or tapered. In some embodiments, slot 126 has one or more of various surface configurations, for example, rough, threaded, arcuate, undulating, porous, semi-porous, dimpled, polished and/or textured.

Shaft 38 includes a surface that defines an opening 132, as shown in FIG. 1 that is configured for movable disposal of latch 40 such that latch 40 can translate through shaft 38 to engage pin 128. In some embodiments, opening 132 may have various cross-section configurations, for example, oval, oblong, triangular, rectangular, square, polygonal, irregular, uniform, non-uniform, variable, tubular and/or tapered.

Figure 11:
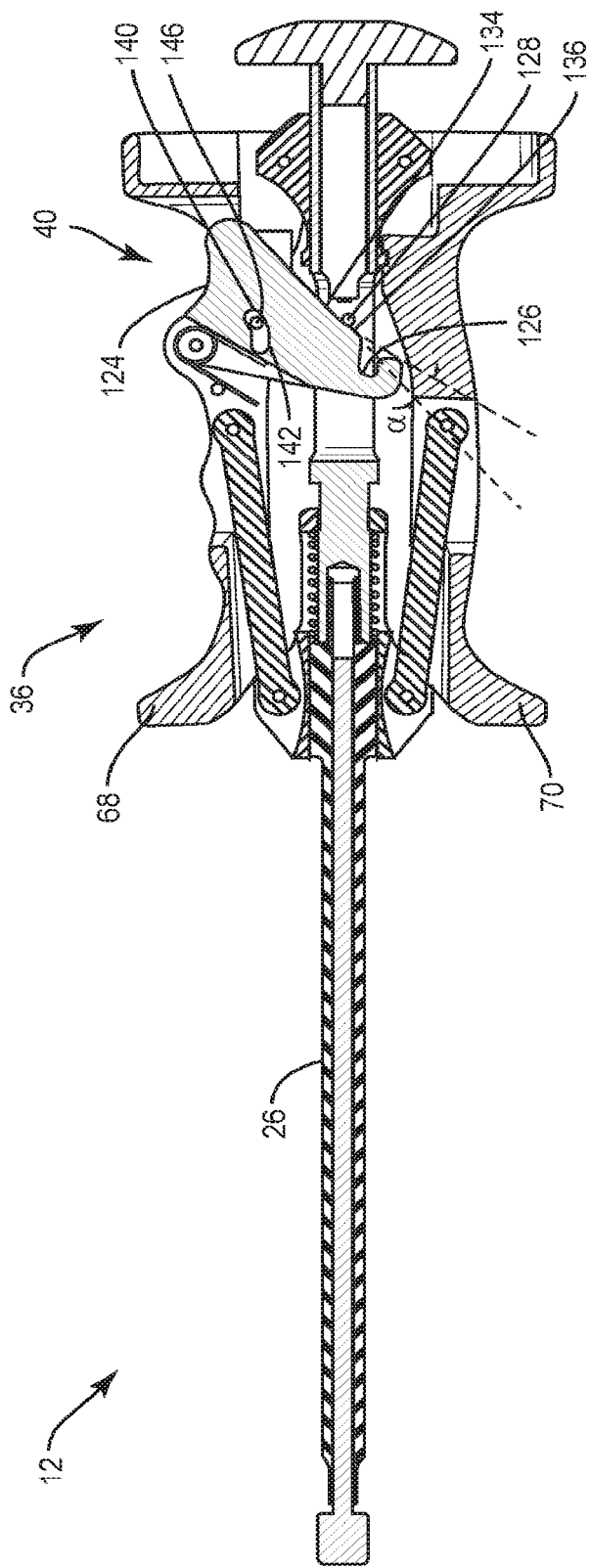
FIG. 11 is a cross section view of the components shown in FIG. 10.
Figure 13:
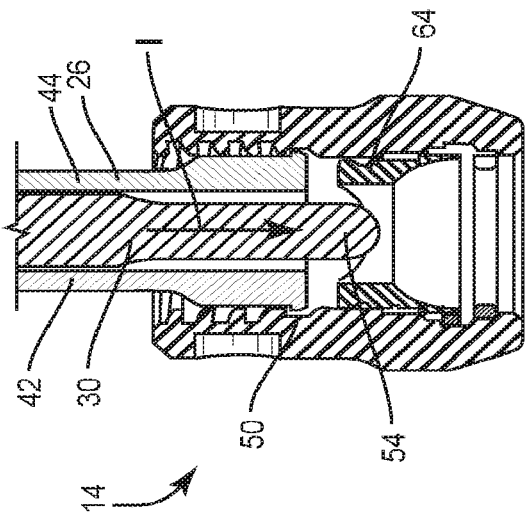
FIG. 13 is a cross section view of the components shown in FIG. 12.

Latch 40 defines a ramp 134 and a ramp 136 disposed at a selected angular orientation α relative to ramp 134, as shown in FIGS. 2, 6, 9 and 11. Ramps 134, 136 are configured for slidable engagement with pin 128 to facilitate movement of actuator 36 relative to shaft 30 between the positions, as described herein. Slidable engagement between ramps 134, 136 and pin 128 is actuated via spring 114. In some embodiments, ramps 134, 136 enable actuator 36 to fully return to the open position from the closed position without actuator 36 becoming disposed in the intermediate position. Spring 62 provides the energy to return actuator 36 to the open position. In some embodiments, ramps 134, 136 are configured to enable inserter 12 to automatically return to the open position from the closed position. In some embodiments, ramps 134, 136 are configured to prevent inserter 12 from capture in the intermediate position via engagement between pin 128 and slot 126, as described herein. Ramps 134, 136 are relatively oriented to form angle α, as shown in FIG. 11. In some embodiments, angle α is in a range from greater than 0 to 90 degrees.

In the open position, as shown by arrows J in FIG. 1, latch 40 is oriented with actuator 36 in the non-locked orientation where pin 128 engages an end surface 138 of latch 40, as shown in FIG. 2. In the intermediate position, as shown by arrows C in FIG. 5, actuator 36 is manually compressed and slot 126 translates relative to pin 128 such that a surface of slot 126 engages pin 128 to orient latch 40 into the locked orientation, as shown in FIG. 6. Latch 40 is depressed, as shown by arrow F in FIG. 9, and spring 114 is biased and pin 128 engages ramp 136, as shown in FIG. 9. In the closed position, as shown by arrows G in FIG. 10, actuator 36 is manually compressed and pin 128 translates from ramp 136 to ramp 134 such that latch 40 is oriented into the non-locked orientation, as shown in FIG. 11.

Ramps 134, 136 enable inserter 12 to automatically return to an open position from the closed position and prevents inserter 12 from capture in the intermediate position. When actuator 36 is further compressed and released, inserter 12 automatically returns to the open position from the closed position. In some embodiments, actuator 36 is further compressed from the closed position and rapidly released to automatically return to the open position. In some embodiments, actuator 36 is further compressed from the closed position and slowly released such that actuator 36 returns to the intermediate position and latch 40 is depressible to return actuator 36 to the open position.

Latch 40 includes a slot 138, as shown in FIG. 6. Slot 138 includes an end, for example, a rotatable limit 140 and an end, for example a rotatable limit 142. Limits 140, 142 are configured to limit the rotation of latch 40 relative to actuator 36. Handle 68 includes an opening 144, as shown in FIG. 5. A pin 146 is configured for disposal within slot 138 and opening 144 such that when latch 40 rotates, pin 146 abuts limits 140, 142. When actuator 36 is in the open position and latch 40 is in the non-locked orientation, pin 146 abuts with limit 142. In the intermediate position, latch 40 is disposed in the locked orientation such that pin 146 abuts limit 142. In the non-locked orientation, latch 40 is depressed via trigger 124 and pin 146 is disposed within an intermediate section 148, as shown in FIG. 9. In the closed position, latch 40 is disposed in the non-locked orientation, and pin 146 abuts limit 140, as shown in FIG. 11.

In operation, handles 68, 70 are movable to the open position, as shown by arrows J in FIG. 1, and latch 40 is disposed with actuator 36 in the non-locked orientation, as shown in FIG. 2. Receiver 14 is loaded into end 22 of inserter 12. In the open position, tabs 42, 44 are in a biased radially inward direction, as shown by arrows B in FIG. 4, and tabs 42, 44 do not engage groove 50 of receiver 14.

Handles 68, 70 of actuator 36 are movable to the intermediate position, as shown by arrows C in FIG. 5, and latch 40 is disposed in the locked orientation, as shown in FIG. 6. Latch 40 locks with pin 128 via slot 126 to prevent handles 68, 70 from opening or closing. In the intermediate position, receiver 14 is secured to end 22 of inserter 12, as shown in FIG. 7. Shaft 30 translates in a direction, for example, axially, as shown by arrow E in FIG. 7 and engages an inner surface of tabs 42, 44 of sleeve 26 to expand tabs 42, 44 to engage groove 50 of receiver 14.

Figure 10:
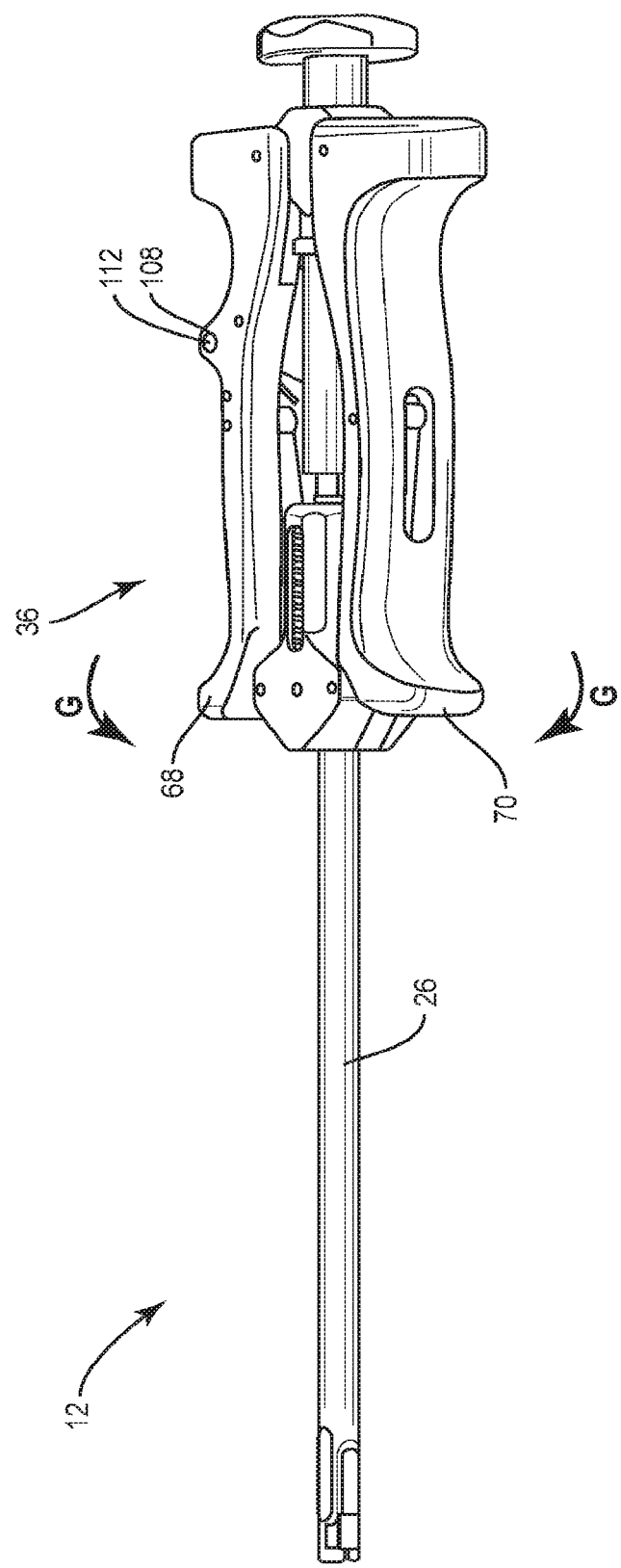
FIG. 10 is a perspective view of the components shown in FIG. 1.

Trigger 124 is depressed, as shown by arrow F in FIG. 9 and handles 68, 70 are compressed, for example, in an inward direction as shown by arrows G in FIG. 10, such that shaft 30 translates axially, as shown by arrow H in FIG. 12 and sleeve 26 remains engaged to groove 50. Handles 68, 70 are movable to the closed position, as shown by arrows G in FIG. 10, and latch 40 is disposable in the non-locked orientation, as shown in FIG. 11. End 54 of shaft 30 drives crown 64 axially, as shown by arrow I in FIG. 13. Handles 68, 70 are further compressed from the closed position and rapidly released to automatically return to the open position, and receiver 14 is released from end 22.

In assembly, operation and use, surgical system 10, is employed with a surgical procedure, for example, a surgical treatment of an applicable condition or injury of an affected section of a spinal column and adjacent areas within a body. In some embodiments, surgical system 10 can be used in any surgical method or technique including open surgery, mini-open surgery, minimally invasive surgery and percutaneous surgical implantation, whereby vertebrae V is accessed, such as through a mini-incision, and possibly also via a sleeve (not shown) that provides a protected passageway to vertebrae V. Once access to the surgical site is obtained, the particular surgical procedure can be performed for treating the spine disorder.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region. Pilot hole(s) (not shown) are made with the selected areas of bone, for example vertebrae for receiving shaft 18.

Handles 68, 70, as described herein, are movable to the open position, as shown by arrows J in FIG. 1, and latch 40 is disposed with actuator 36 in the non-locked orientation, as shown in FIG. 2. Receiver 14 is loaded to end 22 of inserter 12, as described herein, in a direction shown by arrow A in FIG. 3. Handles 68, 70 of actuator 36 are movable to the intermediate position, as shown by arrows C in FIG. 5, and latch 40 is disposed in the locked orientation, as shown in FIG. 6. In the intermediate position, receiver 14 is secured to end 22 of inserter 12, as shown in FIG. 7. Shaft 30 translates axially, as shown by arrow E in FIG. 7 and engages an inner surface of tabs 42, 44 of sleeve 26 to expand tabs 42, 44 to engage groove 50 of receiver 14.

Handles 68, 70 are movable to the closed position, as shown by arrows G in FIG. 10, and latch 40 is disposable in the non-locked orientation, as shown in FIG. 11. Trigger 124 is depressed, as shown by arrow F in FIG. 9 and handles 68, 70 are compressed in an inward direction as shown by arrows G in FIG. 10, such that shaft 30 translates axially, as shown by arrow H in FIG. 12 and sleeve 26 remains engaged to groove 50. In the closed position, end 54 of shaft 30 drives crown 64 axially, as shown by arrow I in FIG. 13. Handles 68, 70 are further compressed from the closed position and rapidly released to automatically return to the open position, and receiver 14 is released from end 22.

Upon completion of a procedure, inserter 12, surgical instruments and/or tools, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, surgical system 10 may include one or a plurality of bone fixation devices, including plates, connectors, spinal rods and/or bone fasteners for use with a single vertebral level or a plurality of vertebral levels. In some embodiments, one or more of bone fixation devices may be engaged with tissue in various orientations, for example, series, parallel, offset, staggered and/or alternate vertebral levels. In some embodiments, one or more bone fixation devices may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 includes an agent, which may be disposed, packed, coated or layered within, on or about the components and/or surfaces of surgical system 10. In some embodiments, the agent may include bone growth promoting material, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Figure 14:
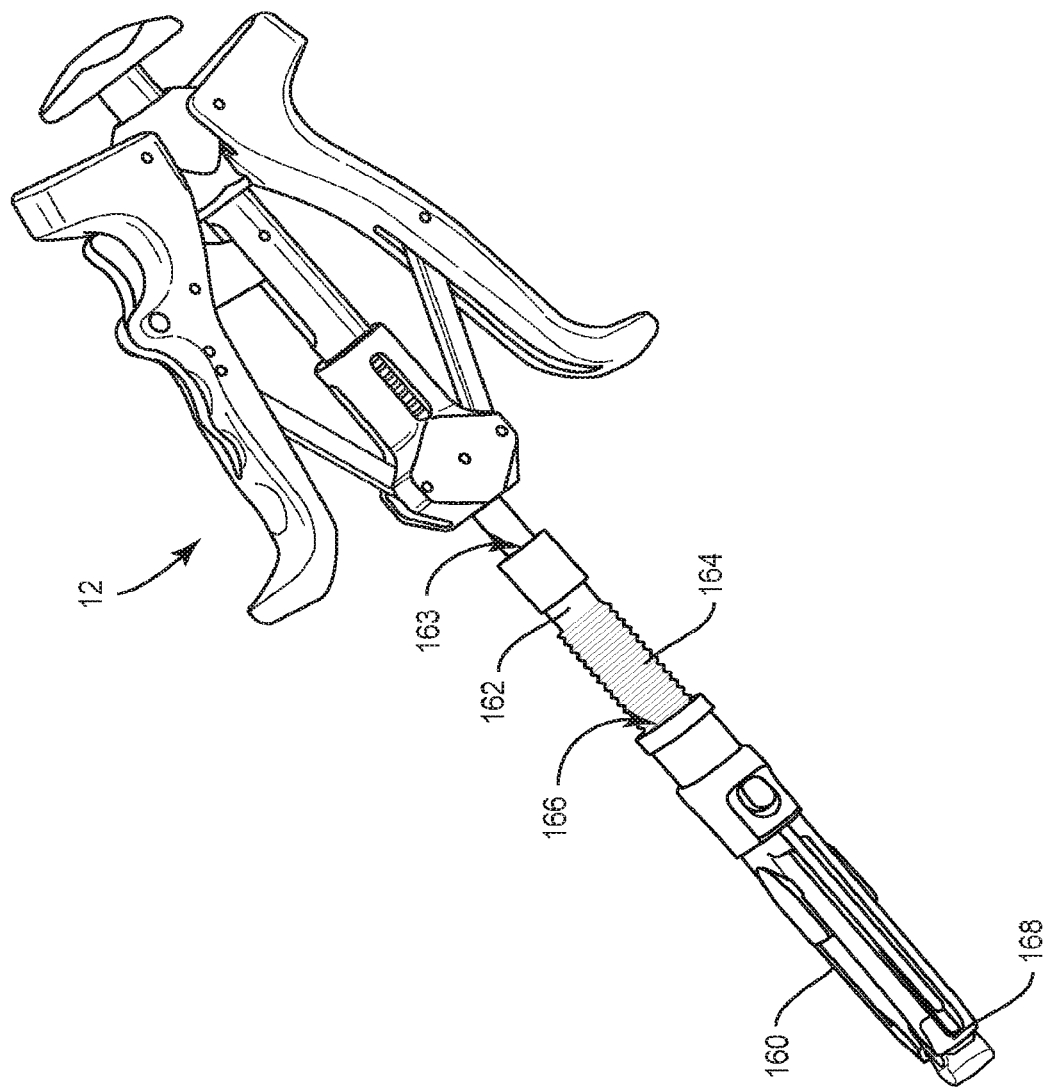
FIG. 14 is a perspective view of components of one embodiment of a surgical system in accordance with the principles of the present disclosure.

In some embodiments, as shown in FIG. 14, surgical system 10 includes an implant support, for example, an extender 160 that includes a spinal rod reducer 162. Extender 160 and reducer 162 are configured for use with inserter 12. In some embodiments, extender 160 is oriented for manipulation, alignment and/or capture of receiver 14 and reducer 162 is configured to dispose a spinal rod (not shown) with receiver 14. Reducer 162 includes an inner surface that defines a passageway 163 that is configured for disposal of sleeve 26 of inserter 12. An outer surface 164 is threaded to an inner surface of extender 160 that defines a passageway 166. Reducer 162 is rotated to translate reducer 162 axially, in a proximal or distal direction relative to inserter 12 and/or extender 160. Reducer 162 is translated such that an end surface 168 engages the spinal rod in a configuration to move the spinal rod relative to receiver 14 to drive and/or reduce the spinal rod into receiver 14.

Figure 15:
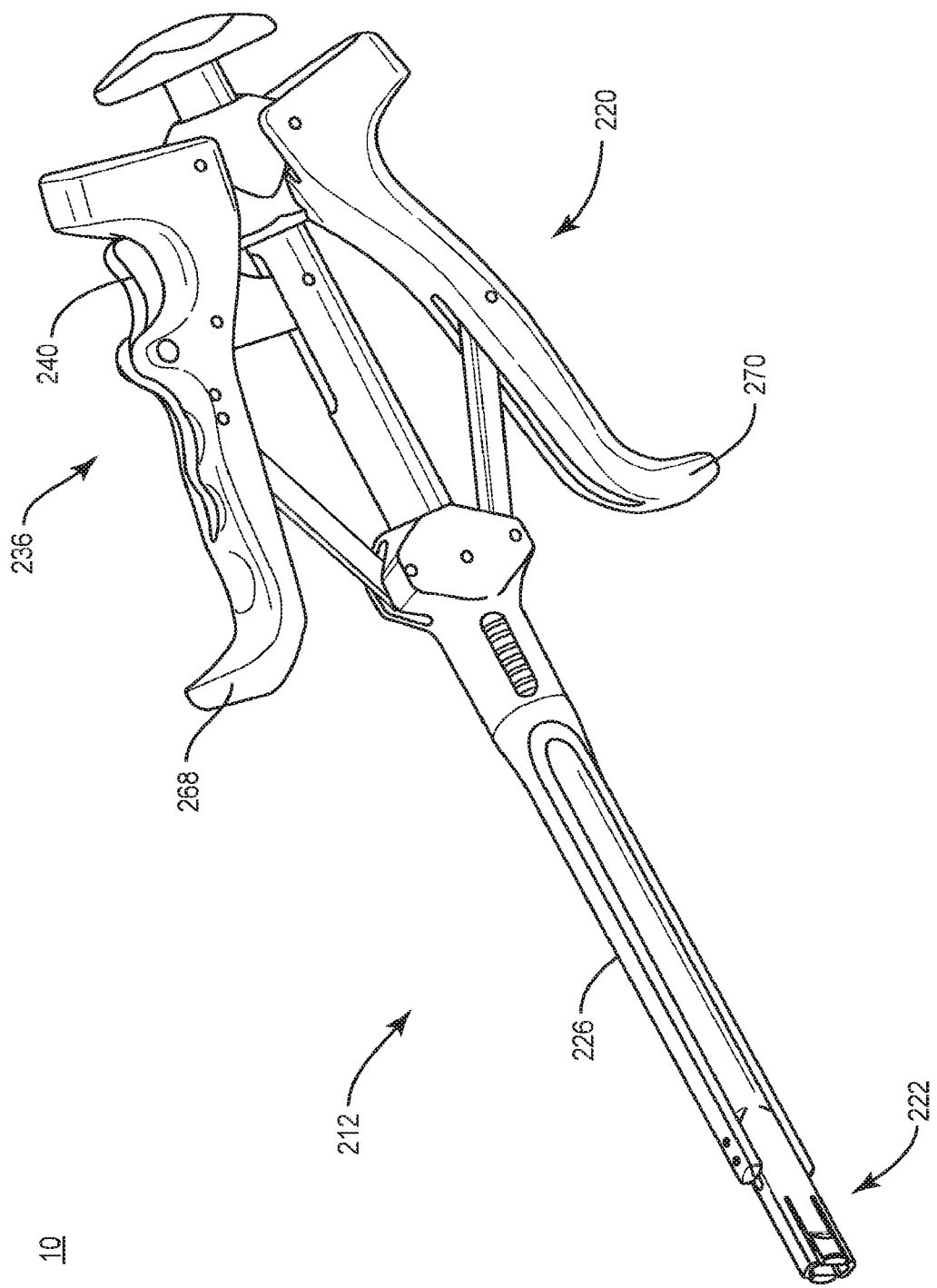
FIG. 15 is a perspective view of components of one embodiment of a surgical system in accordance with the principles of the present disclosure.
Figure 16:
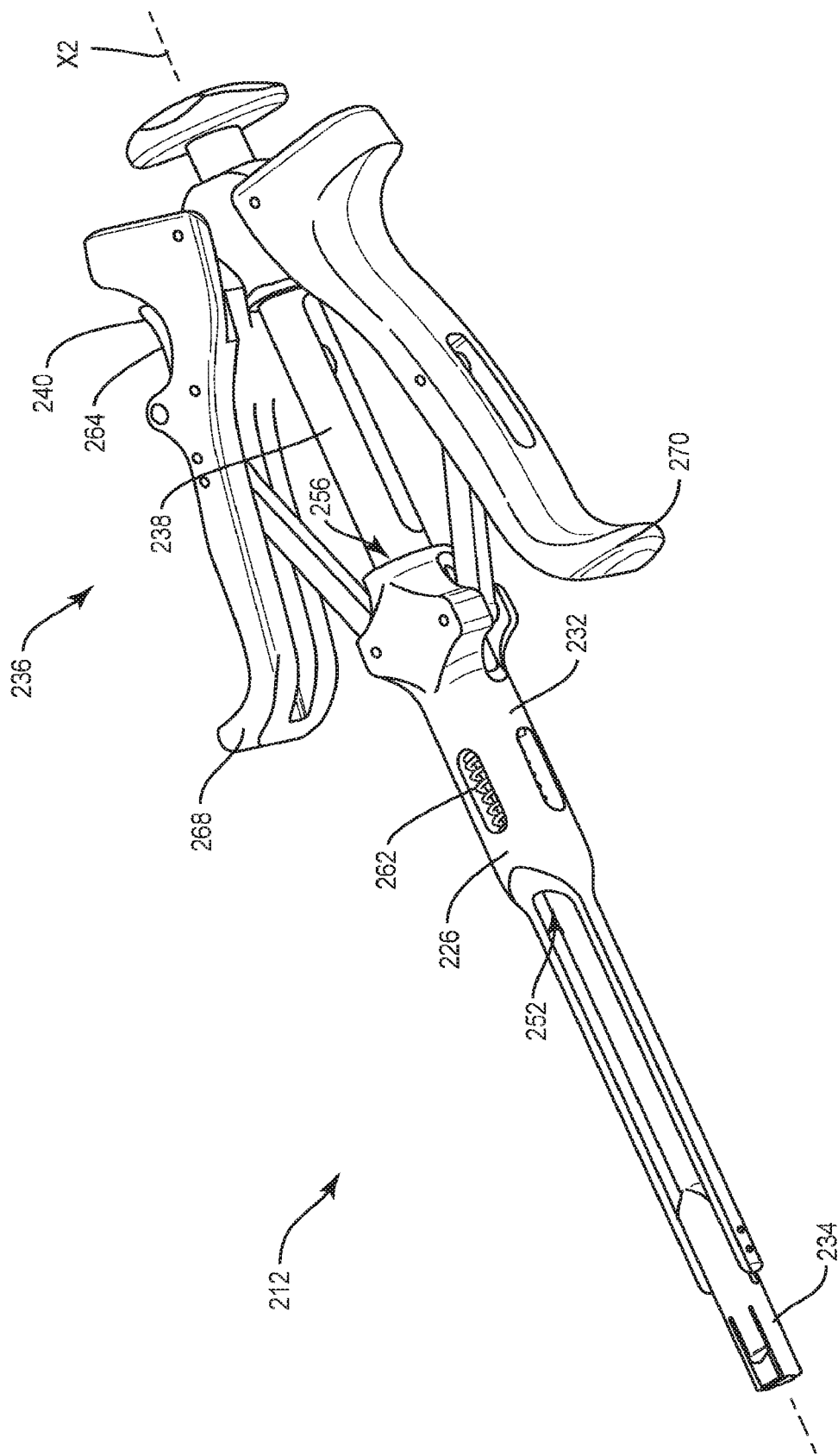
FIG. 16 is a perspective view of the components shown in FIG. 15.
Figure 17:
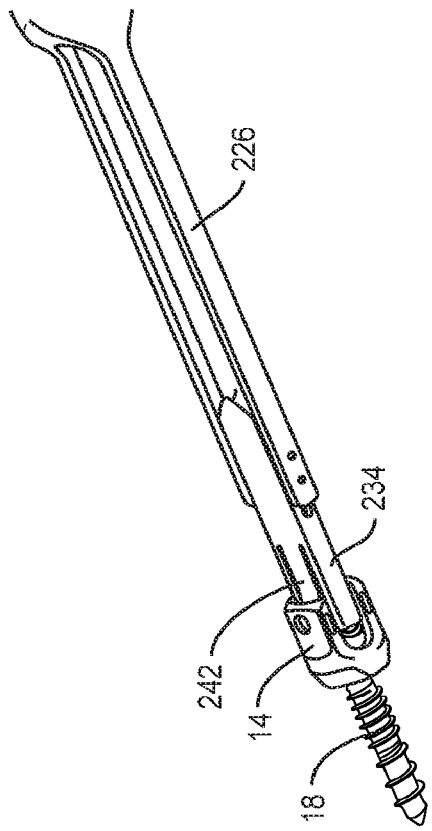
FIG. 17 is a break away view of components of one embodiment of a surgical system in accordance with the principles of the present disclosure.

In some embodiments, as shown in FIGS. 15-22, surgical system 10, includes an inserter 212, similar to inserter 12 described herein, configured for use with receiver 14, as shown in FIG. 17. Inserter 212 includes a proximal end 220 and a distal end 222, as shown in FIG. 15. Inserter 212 extends along and defines a longitudinal axis X2, as shown in FIG. 16.

Figure 18:
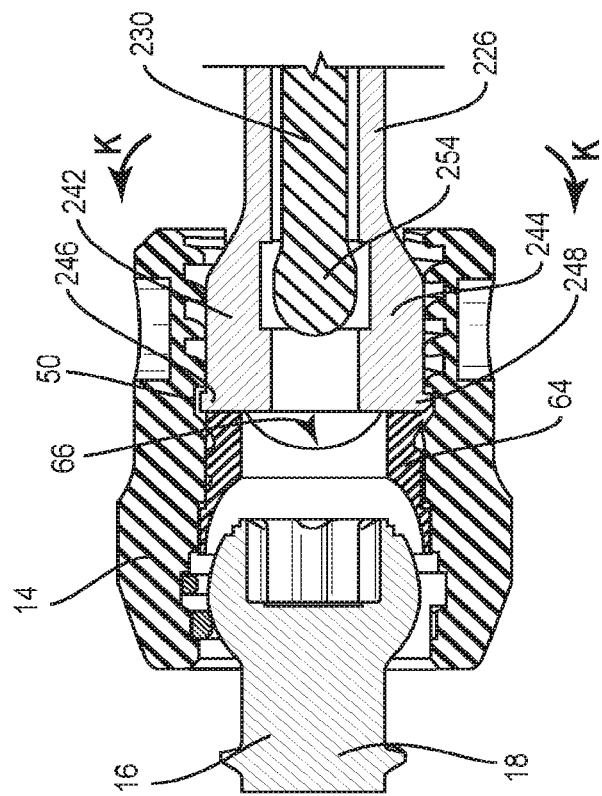
FIG. 18 is a cross section view of the components shown in FIG. 17.
Figure 20:
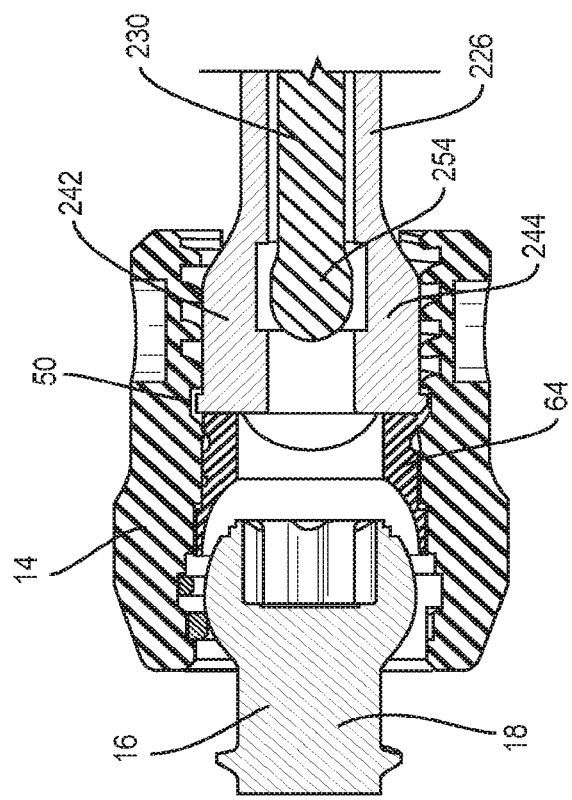
FIG. 20 is a cross section view of the components shown in FIG. 17.

Inserter 212 includes an outer sleeve 226 and an inner shaft 230, as shown in FIG. 18. Sleeve 226 and shaft 230 are configured for engagement to receiver 14. Sleeve 226 includes an end 232 and an end 234. In some embodiments, sleeve 226 may have various cross-section configurations, for example, oval, oblong, triangular, rectangular, square, polygonal, irregular, uniform, non-uniform, variable, tubular and/or tapered.

End 232 is configured for engagement to an actuator 236, similar to actuator 36, as shown in FIG. 18. Actuator 236 is movable relative to sleeve 226, as described herein. An outer shaft 238 is disposed at end 232 and is configured for engagement to actuator 236 and a latch 240, similar to latch 40 described herein, as shown in FIG. 16. In some embodiments, shaft 238 may have various cross-section configurations, for example, oval, oblong, triangular, rectangular, square, polygonal, irregular, uniform, non-uniform, variable, tubular and/or tapered.

End 234 is configured for engagement to an inner surface of receiver 14, as shown in FIG. 17. End 234 is expandable to engage the inner surface of receiver 14 to secure receiver 14 to inserter 12, as shown in FIG. 17. End 234 includes a spring tab 242 and a spring tab 244. Tab 242 opposes tab 244. Tabs 242 and 244 are flexible, biased radially inward and are expandable to engage the inner surface of receiver 14 and to secure receiver 14 to inserter 212. Tab 242 includes an outer surface that defines a projection 246 and tab 244 includes an outer surface that defines a projection 248, as shown in FIG. 18. Groove 50 of receiver 14 is configured for engagement to projections 246 and 248, as shown in FIG. 18. In some embodiments, sleeve 226 includes one or more spring tabs.

Figure 19:
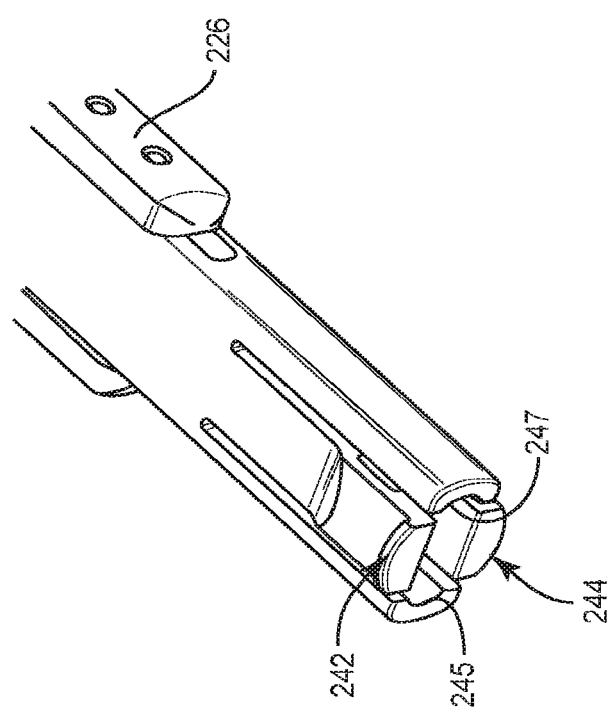
FIG. 19 is an enlarged break away view of the components shown in FIG. 15.

End 234 includes an inner surface that defines a groove 245 and a groove 247, as shown in FIG. 19. Grooves 245, 247 are configured for engagement to an end 254 of shaft 230 to facilitate engagement of crown 64, as described herein.

Shaft 230 includes an end 252 and end 254, as shown in FIGS. 16 and 18. Shaft 230 is in co-axial alignment relative to sleeve 226 and extends along longitudinal axis X2, as shown in FIG. 16. Shaft 230 translates relative to sleeve 226 to secure receiver 14 to shaft 18, as described herein. Shaft 230 is configured to expand sleeve 226 into engagement to the inner surface of receiver 14 to secure receiver 14. In some embodiments, shaft 230 may have various cross-section configurations, for example, oval, oblong, triangular, rectangular, square, polygonal, irregular, uniform, non-uniform, variable, tubular and/or tapered.

End 252 is configured for engagement to an end 256 of shaft 238, as shown in FIG. 16, similar to end 52 engagement to end 56 of shaft 38, as described above with regard to inserter 12. Shaft 230 is fixed to shaft 238 and shaft 230 is movable relative to sleeve 226. A biasing member, for example, a spring 262 is configured for disposal about end 256, as shown in FIG. 16 and is configured to provide energy in an axial direction to facilitate return movement of shaft 230 when actuator 236 is released, as described herein.

End 254 is configured for engagement to crown 64 disposed within cavity 66 of receiver 14, as shown in FIG. 18. Crown 64 is configured for locking receiver 14 to shaft 18, as described herein. In some embodiments, end 254 may have various cross-section configurations, for example, oval, oblong, triangular, rectangular, square, polygonal, irregular, uniform, non-uniform, variable, tubular and/or tapered.

End 220 of inserter 212 includes actuator 236, as shown in FIG. 15. Actuator 236 is rotatable relative to sleeve 26 and is disposable between an open position including a non-locked orientation, an intermediate position including a locked orientation and a closed position including a non-locked orientation, as described herein. Actuator 236 includes a pair of lever handles 268, 270, as shown in FIG. 15 that are rotatable relative to sleeve 226.

Latch 240 is connected to actuator 236 in a non-locked orientation such that actuator 236 is movable relative to sleeve 226 in the open position and closed position, and a locked orientation such that actuator 236 is fixed relative to sleeve in the intermediate position. Latch 240 is connected to actuator 236 via handle 268, in the same manner as latch 40 is connected to actuator 36, described above with regard to FIGS. 1-13.

In operation, handles 268, 270 are movable to the open position, and latch 240 is disposed with actuator 236 in the non-locked orientation. Receiver 14 is loaded into end 222 of inserter 212. In the open position, tabs 242, 244 are in a biased radially inward direction, as shown by arrows K in FIG. 18, and tabs 242, 244 do not engage groove 50 of receiver 14.

Figure 21:
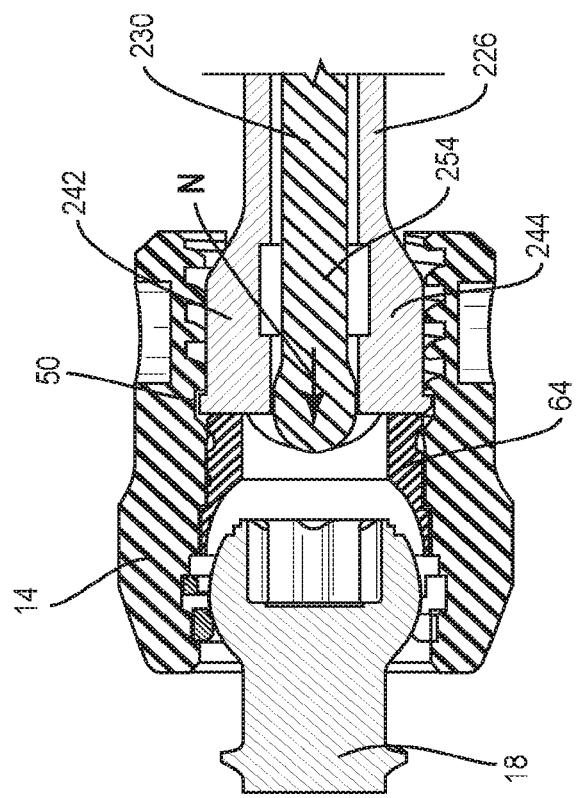
FIG. 21 is a cross section view of the components shown in FIG. 17.
Figure 22:
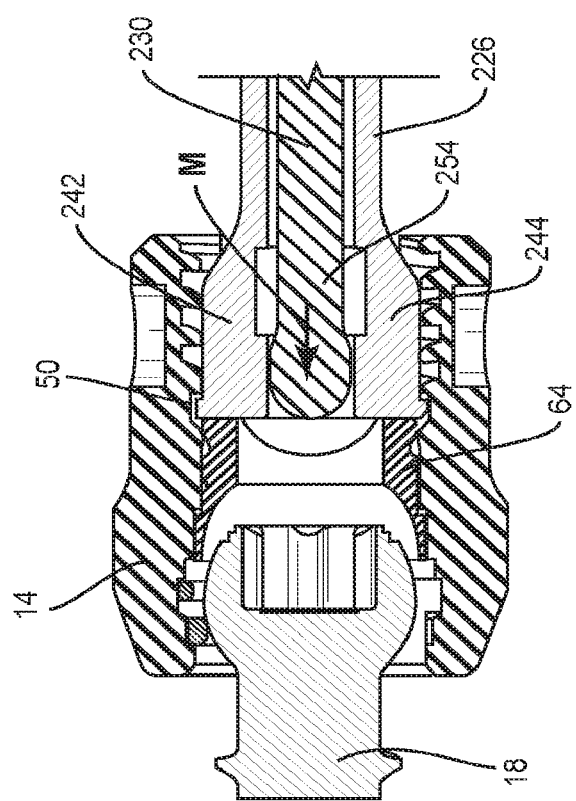
FIG. 22 is a cross section view of the components shown in FIG. 17.

Handles 268, 270 of actuator 236 are movable to the intermediate position, and latch 240 is disposed in the locked orientation. In the intermediate position, receiver 14 is secured to end 222 of inserter 212, as shown in FIG. 21. Shaft 230 translates in a direction, for example, axially, as shown by arrow M in FIG. 21 and end 254 engages grooves 245, 247 and inner surfaces of tabs 242, 244 of sleeve 226 to expand tabs 242, 244 to engage groove 50 of receiver 14.

Handles 268, 270 are movable to the closed position, and latch 240 is disposable in the non-locked orientation. A trigger 264 of latch 240 is depressed and handles 268, 270 are compressed, for example, in an inward direction, such that shaft 230 translates axially, as shown by arrow N in FIG. 22 and sleeve 226 remains engaged groove 50. End 254 of shaft 230 drives crown 64 axially, as shown by arrow N in FIG. 22. Handles 268, 270 are further compressed from the closed position and rapidly released to automatically return to the open position, and receiver 14 is released from end 222.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical inserter comprising:
an outer sleeve having a distal portion, the distal portion including at least one expandable projection being engageable with an inner groove of a spinal rod receiver of a bone fastener, the spinal rod receiver comprising a crown;
an inner shaft having a distal portion being engageable with the distal portion of the outer sleeve to expand the at least one expandable projection into the inner groove to capture the spinal rod receiver;
the inner shaft being engageable with the crown for connecting the spinal rod receiver with the surgical inserter; and
the distal portion of the inner shaft including a tapered configuration and a tip engageable with the crown.

2. The surgical instrument of claim 1, wherein the distal portion of the inner shaft is translatable relative to the distal portion of the outer shaft.

3. The surgical instrument of claim 1, wherein the distal portion of the outer sleeve is biased radially inward.

4. The surgical instrument of claim 1, wherein the distal portion of the outer sleeve includes at least one spring tab biased radially inward and expandable to engage the inner groove and capture the spinal rod receiver.

5. The surgical instrument of claim 1, wherein the distal portion of the outer sleeve is engageable with the spinal rod receiver for snap fit assembly.

6. The surgical instrument of claim 1, wherein the at least one expandable projection includes a first expandable projection and a second expandable projection.

7. The surgical instrument of claim 1, wherein the distal portion of the outer sleeve includes opposing spring tabs biased radially inward and expandable to engage the inner groove and capture the spinal rod receiver.

8. A surgical inserter comprising:
an outer sleeve having a distal portion, the distal portion including a first expandable projection and a second expandable projection being engageable with an inner groove of a spinal rod receiver of a bone fastener; and
an inner shaft having a distal portion being engageable with the distal portion of the outer sleeve to expand the first expandable projection and the second expandable projection into the inner groove to capture the spinal rod receiver;
wherein the spinal rod receiver comprises a crown and the distal portion of the inner shaft comprises an inwardly tapered configuration and a tip engageable with the crown, and
wherein the distal portion of the outer sleeve is engageable with the spinal rod receiver for a snap fit assembly.

9. The surgical inserter of claim 8, wherein the first expandable projection and the second expandable projection are biased radially inward.

10. The surgical inserter of claim 8, wherein the distal portion of the outer sleeve includes opposing spring tabs biased radially inward and expandable to engage the inner groove and capture the spinal rod receiver.

11. The surgical inserter of claim 8, wherein the inner shaft is engageable with the crown for connecting the spinal rod receiver with the surgical instrument.

12. The surgical system of claim 8, wherein each of the first expandable projection and the second expandable projection are disposed in a spaced apart relation to the crown of the spinal rod receiver when the first expandable projection and the second expandable projection are engaged with the inner groove of the spinal rod receiver and when the inner shaft is engaged with the crown.

13. A surgical system comprising:
a bone fastener shaft configured for fixation to vertebral tissue;
a spinal rod receiver configured for connection to the bone fastener shaft and comprising a crown disposed within a cavity of the spinal rod receiver; and
a surgical instrument including an outer sleeve and an inner shaft,
a distal portion of the outer sleeve including at least one expandable projection being engageable with an inner groove of the spinal rod receiver, and
a distal portion of the inner shaft being engageable with the distal portion of the outer sleeve to expand the at least one expandable projection into the inner groove to capture the spinal rod receiver,
wherein the distal portion of the inner shaft comprising a tapered configuration and a round tip for connecting the spinal rod receiver with the surgical instrument;
wherein the distal portion of the inner shaft is disposed in an at least partially spaced apart relation to an interior of the outer sleeve and the round tip extends beyond the at least one expandable projection and is engageable with the concave surface of the crown when the at least one expandable projection is engaged with the inner groove of the spinal rod receiver.

14. The surgical system of claim 13, wherein the distal portion of the inner shaft is translatable relative to the distal portion of the outer-shaft sleeve.

15. The surgical system of claim 13, wherein the distal portion of the outer sleeve includes at least one spring tab biased radially inward and expandable to engage the inner groove and capture the spinal rod receiver.

16. The surgical system of claim 13, wherein the distal portion of the outer sleeve includes opposing spring tabs biased radially inward and expandable to engage the inner groove and capture the spinal rod receiver.

17. The surgical system of claim 13, wherein the inner shaft is disposed in an at least partially spaced apart relation to an interior of the at least one expandable projection when the at least one expandable projection is engaged with the inner groove of the spinal rod receiver.

18. The surgical system of claim 13, wherein the at least one expandable projection comprises two pairs of oppositely disposed expandable projections.

19. The surgical system of claim 13, wherein the at least one expandable projection comprises four expandable projections; each expandable projection being perpendicularly disposed to an adjacent expandable projection.

20. The surgical system of claim 13, wherein the distal portion of the inner shaft is disposed in an at least partially spaced apart relation to the at least one expandable projection when the at least one expandable projection is engaged with the inner groove of the spinal rod receiver.

* * * * *